US008133740B1

(12) United States Patent
DeVol et al.

(10) Patent No.: US 8,133,740 B1
(45) Date of Patent: Mar. 13, 2012

(54) COLORIMETRIC DETECTION OF URANIUM IN WATER

(75) Inventors: Timothy A. DeVol, Clemson, SC (US);
Amy E. Hixon, Piedmont, SC (US);
David P. DiPrete, Evans, GA (US)

(73) Assignees: Clemson University Research Foundation, Anderson, SC (US);
Savannah River Nuclear Solutions, LLC, Aiken, SC (US)

(*) Notice: Subject to any disclaimer, the term of this patent is extended or adjusted under 35 U.S.C. 154(b) by 112 days.

(21) Appl. No.: 12/543,856

(22) Filed: Aug. 19, 2009

Related U.S. Application Data

(60) Provisional application No. 61/089,994, filed on Aug. 19, 2008.

(51) Int. Cl.
*G01N 33/20* (2006.01)
(52) U.S. Cl. ............. 436/82; 436/73; 436/164; 436/166
(58) Field of Classification Search .................... 436/82, 436/73, 164, 166
See application file for complete search history.

(56) References Cited

U.S. PATENT DOCUMENTS

| | | |
|---|---|---|
| 4,127,499 A | 11/1978 | Chen et al. |
| 4,198,568 A | 4/1980 | Robbins et al. |
| 4,275,031 A | 6/1981 | Fischer et al. |
| 4,349,350 A | 9/1982 | Fitoussi et al. |
| 4,568,649 A | 2/1986 | Bertoglio-Matte |
| 4,574,072 A | 3/1986 | Horowitz et al. |
| 4,835,107 A | 5/1989 | Horowitz et al. |
| 5,100,585 A | 3/1992 | Horowitz et al. |
| 5,190,881 A | 3/1993 | McKibbin |
| 5,281,631 A | 1/1994 | Horowitz et al. |
| 5,346,618 A | 9/1994 | Horowitz et al. |
| 5,466,930 A | 11/1995 | Schlenoff |
| 5,603,834 A | 2/1997 | Rogers et al. |
| 5,618,851 A | 4/1997 | Trochimcznk et al. |
| 5,637,506 A | 6/1997 | Goken et al. |
| 5,651,883 A | 7/1997 | Horowitz et al. |
| 5,707,525 A | 1/1998 | Rogers et al. |
| 6,107,098 A | 8/2000 | Kalinich |
| 6,139,749 A | 10/2000 | Goken et al. |
| 6,165,367 A | 12/2000 | Partridge |
| 6,303,936 B1 | 10/2001 | DeVol et al. |
| 7,157,022 B2 | 1/2007 | Horwitz et al. |

OTHER PUBLICATIONS

Development of a Colorimetric Test for Uranium J.F. Kalinich and D.E. McClain NATO RTG-099 2005.*
Uranium and Radon in Groundwater K. Skeppstrom and B. Olofsson European Water 17/18: 51-62, 2007.*

(Continued)

*Primary Examiner* — Robert J Hill, Jr.
*Assistant Examiner* — Dwan A Gerido
(74) *Attorney, Agent, or Firm* — Dority & Manning, P.A.

(57) ABSTRACT

Disclosed are methods, materials and systems that can be used to determine qualitatively or quantitatively the level of uranium contamination in water samples. Beneficially, disclosed systems are relatively simple and cost-effective. For example, disclosed systems can be utilized by consumers having little or no training in chemical analysis techniques. Methods generally include a concentration step and a complexation step. Uranium concentration can be carried out according to an extraction chromatographic process and complexation can chemically bind uranium with a detectable substance such that the formed substance is visually detectable. Methods can detect uranium contamination down to levels even below the MCL as established by the EPA.

29 Claims, 4 Drawing Sheets

OTHER PUBLICATIONS

Highly Accurate Determination of Trace Amounts of Uranium in Standard Reference Materials by Spectrophotometry with Chlorophosphonazo III After Complete Separation by Anion and Cation Exchange Chromatography F.W.E. Strelow and T.N. van der Walt Fresenium Z. Anal Chem. 306, 110-114, 1981.*

Bouvier-Capely et al., "The use of calyx[6]arene molecules for actinides analysis in urine: an alternative to current procedures," *54th Annual Radiobioassay and Radiochemical Measurements Conference*, Oct. 27-31, 2008, Destin, FL, 6 pages.

DeVol et al., "Influence of Radionuclide Adsorption on Detection Efficiency and Energy Resolution for Flow-Cell Radiation Detectors," *IEEE Transactions on Nuclear Science*, vol. 43, No. 3, Jun. 1996, pp. 1310-1315.

Egorov et al., "Radionuclide Sensors Based on Chemically Selective Scintillating Microspheres: Renewable Column Sensor for Analysis of $^{99}$Tc in Water," *Analytical Chemistry*, vol. 71, No. 23, Dec. 1, 1999, pp. 5420-5429.

Heimbuch et al., "The Assay of Alpha- and Beta-Emitters by Means of Scintillating Ion-Exchange Resins," *Proceedings of the Symposium on Radioisotope Sample Measurement Techniques in Medicine and Biology Held by the International Atomic Energy Agency in Vienna*, May 24-28, 1965, pp. 505-519.

Izatt et al., "The Application of Molecular Recognition Technology (MRT) in the Nuclear Power Cycle: From Uranium Mining and Refining to Power Plant Waste Separation and Recovery, as well as Element Analysis and Isotope Purification," *WM2009 Conference*, Phoenix, AZ, Mar. 1-5, 2009, pp. 1-11.

Li et al., "Ion Exchange Using a Scintillating Polymer with a Charged Surface," *Analytical Chemistry*, vol. 66, No. 6, Mar. 15, 1994, pp. 824-829.

Ludwick, J. Donald, "The Analysis of Plutonium-241 in Urine," *Health Physics*, Pergamon Press 1961, vol. 6, pp. 63-65.

Maischak et al., "Solid-Phase Extraction for the Separation of Actinides from Radioactive Waste," *WM01 Conference*, Feb. 25-Mar. 1, 2001, Tucson, AZ, 9 pages.

Presentation—"Analysis of U in urine using URALIX column," Procedure U/URALIX, Feb. 26, 2008, 17 pages.

Related U.S. Patent Application Form.

* cited by examiner

COLORIMETRIC DETECTION OF URANIUM IN WATER

CROSS REFERENCE TO RELATED APPLICATION

The present application claims filing benefit of U.S. Provisional Patent Application Ser. No. 61/089,994 having a filing date of Aug. 19, 2008.

FEDERALLY SPONSORED RESEARCH AND DEVELOPMENT

The United States Government may have rights in this disclosure pursuant to U.S. Department of Energy Grant Number DE-FG02-07ER64411.

BACKGROUND

Uranium is a naturally occurring radioactive element widely distributed among igneous rocks and oxide minerals. There are three naturally occurring uranium isotopes, $^{238}$U, $^{235}$U, and $^{234}$U. All three natural isotopes undergo radioactive decay by alpha emission accompanied by weak gamma radiation. Although all three uranium isotopes are present in groundwater, $^{238}$U and $^{234}$U predominate on an activity basis. Uranium ore, composed of uranium-containing minerals such as uraninite, $O_3O_8$, and carnotite, $K_2(UO_2)_2(VO_4)_2 \cdot 3H_2O$, are a mixture of $^{238}$U, $^{235}$U, $^{234}$U, and decay progeny, and are chemically stable under reducing conditions. However, if oxidants are introduced to the surface of these minerals, oxidative dissolution occurs. Upon dissolution, uranium can be found in groundwater at elevated concentrations and can find its way into water supplies.

It has been estimated that 0.3-6% of all ingested uranium is absorbed and deposited in the bones, kidneys, liver, and other soft tissues (Taylor and Taylor, 1997). This may result in nephritis, kidney damage, and an increased cancer risk. To ensure that there is insignificant risk to human health over a lifetime, the Environmental Protection Agency (EPA) regulation for public water systems sets the maximum contaminant level (MCL) for uranium at 30 µg/L, effective Dec. 8, 2003.

Methods for determining uranium levels in various types of samples have been developed. For instance, U.S. Pat. No. 4,198,568 to Robbins, et al. teaches uranium determination in aqueous samples through ultraviolet light-induced phosphorescence of the uranium. U.S. Pat. No. 5,190,881 to McKibbin teaches alpha-spectrometry methods to measure uranium content in biological fluids. U.S. Pat. No. 4,349,350 to Fitoussi, et al. teaches that uranium in an organic solvent can be determined by the addition of excess dialkyl dithiophosphoric acid to the organic solvent/uranium solution following which the uranium is converted to a mixed compound complex. The optical density of the solvent containing the complex is then measured to determine the concentration of the organic solvent and the uranium content in the complex. U.S. Pat. No. 6,107,098 to Kalinich discloses a method including mixing a uranium-containing biological sample with a buffer, one or more masking agents, and a solubilizing compound to form a uranium-containing metal binding complex composition. This composition is then combined with a pyridylazo indicator dye. The increase in absorbance due to the complexation of uranium with the dye is then determined with a spectrophotometer or a colorimeter.

Despite such advances in the art, groundwater analysis for uranium content can still be conducted only by a certified radiochemistry laboratory, of which there are very few (believed to be about five) in the United States. Problems with attempts to develop more cost effective, simple uranium detection methods have generally centered around two difficulties; the first being that methods require extensive sample preparation before analysis, and the second being that uranium determination procedures currently require elaborate instrumentation.

While the above-described methods and materials provide certain advances in the art, room for improvement and further advances exist. For instance, a consumer-based test to detect uranium in drinking/groundwater that is rapid, accurate, does not require extensive sample preparation, and requires little or no technical training to carry out would be of great benefit.

SUMMARY

According to one embodiment, disclosed is a method for determining the presence or quantity of uranium in an aqueous test sample, for instance in test sample of natural waters such as groundwater, surface water, rainwater, etc. In one embodiment, disclosed methods can be utilized for determining the presence or quantity of uranium in drinking water, i.e., treated or untreated groundwater and/or treated surface water. For example, a method can include concentrating uranium of an aqueous test sample to form a concentrated uranium sample and complexing the uranium with a detectable substance. The complex of the uranium and the detectable substance can then be visually detected to obtain information with regard to the presence or quantity of the uranium in the aqueous test sample.

Concentration of the uranium can be carried out via, e.g., a chromatography process including, without limitation, an extraction chromatography process, a liquid-liquid extraction process, an ion exchange process, and the like.

Also disclosed herein are systems for detecting the presence or quantity of uranium in an aqueous test sample. For example, a system can include a uranium concentrator such as an extraction chromatography column, an ion exchange column, or the like. A system can also include a detectable substance that forms a visibly detectable complex with uranium. Beneficially, disclosed systems can be portable.

In one preferred embodiment, the detectable substance is Br-PADAP.

Suitable extractants for use in an extraction chromatography process can include, for example, a diamyl amylphosphonate extractant, a dyglycolamide extractant, a phosphonic acid extractant, a tricarboxylic calix[6]arene, and a trishydroxamic calix[6]arene.

BRIEF DESCRIPTION OF THE FIGURES

A full and enabling description of the presently disclosed subject matter, including the best mode thereof, to one of ordinary skill in the art, is set forth more particularly in the remainder of the specification, including reference to the accompanying Figures, in which.

DETAILED DESCRIPTION OF REPRESENTATIVE EMBODIMENTS

Figure 1:
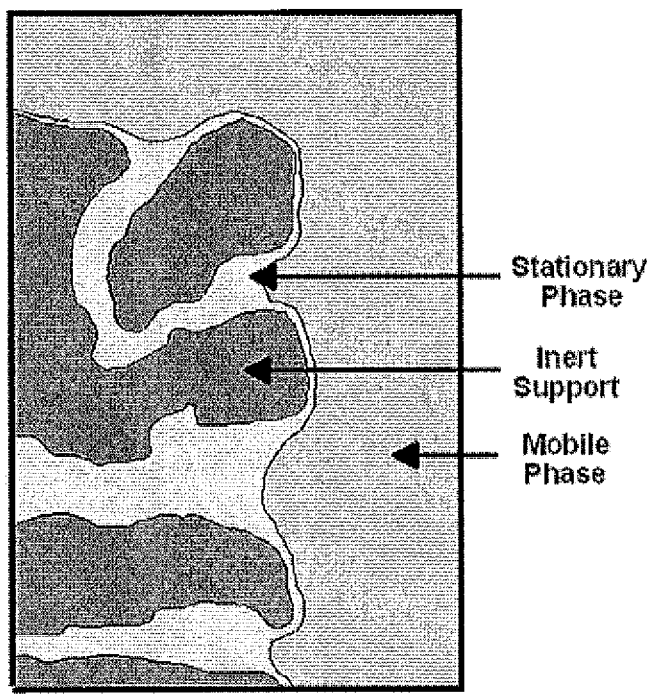
FIG. 1 is a schematic representation of an extraction chromatography method as may be utilized to concentrate uranium of an aqueous test sample.

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made to the disclosed subject matter without departing from the scope or spirit of the disclosure. For instance, features illustrated or described as part of one embodiment, may be used with another embodiment to yield a still further embodiment.

In general, disclosed herein are methods, materials and systems that can be used to determine qualitatively or quantitatively the level of uranium contamination in an aqueous sample. Beneficially, disclosed systems are relatively simple and cost-effective. In one preferred embodiment, disclosed systems can be utilized by consumers having little or no training in chemical analysis techniques. For instance, disclosed methods can provide visual qualitative or quantitative results with regard to uranium contamination of natural waters, and thus need not require the utilization of expensive instrumentation for determination of results. Moreover, disclosed methods can detect uranium contamination down to levels even below the MCL as established by the EPA. For instance, disclosed methods can detect uranium in groundwater with an overall detection limit as low as about 21 µg/L.

Disclosed methods incorporate two processes for uranium detection: concentration and colorimetric detection. The concentration step can provide a sample having an increase in concentration of uranium from an inittial water sample. In one embodiment, the concentration step can also provide a route to separation of the uranium from other metals in the sample that could otherwise interfere with the detection method.

The colorimetric detection step can include complexing the uranium of a sample with a detectable substance so as to enable detection. In one preferred example, the detection can be via an optical detection regime based upon visual results.

While much of the following is directed to methods including an initial concentration step followed by a complexing step, it should be understood that steps of disclosed methods need not be carried out in any particular order or even sequential to one another. For instance, a step of concentrating uranium from a water sample can be carried out either prior to, during, or following the formation of a complex including uranium and a detectable substance, and the disclosed subject matter is not in any way limited to carrying out the steps of the disclosed process in any particular order.

Concentration methods encompassed by the present disclosure include methods that can concentrate uranium contained in a water sample, and in certain embodiments, can separate uranium from other metals that can interfere with detection methods. In one preferred embodiment, an extraction method can be utilized. However, any chromatography method as is generally known in the art can alternatively be utilized including, without limitation, an extraction chromatography method, an ion extraction method, a liquid-liquid extraction method, or the like can be used that can concentrate the uranium from a starting aqueous sample. Moreover, an extraction chromatography method can be a solvent-based extraction method, a solid phase extraction method, or any other suitable extraction method as is generally known in the art.

In general, an extraction chromatography method can utilize a device, e.g., an extraction column, which functions as a concentrator and can include an extractant that binds uranium of a test sample. By way of example, when considering a solvent-based extraction chromatographic method, an extractant can be a component of an organic stationary phase contained on a solid phase. In another embodiment, a solid-phase extraction method can be utilized, in which an extractant can be integral to or directly bound to the solid phase of a concentration device such as an extraction column.

FIG. 1 schematically illustrates one embodiment of an extraction chromatography method as may be utilized. In general, extraction chromatography involves a support phase, a stationary phase and a liquid phase (a.k.a. the mobile phase). A support phase can be, as in the illustrated embodiment, a porous bead as may be packed in an extraction column. Disclosed subject matter is not limited to utilization of a porous bead support phase, however, and any suitable support phase can be used, including monolithic porous support phase, fibrous support phase, a nonporous support phase, and so forth. A support phase can be formed of any suitable material as is known in the art. For example, silica-based macroporous materials, cross-linked polymer-based materials, and the like. Exemplary support phase materials can include, without limitation, cross-linked polysaccharides, such as dextran or synthetic polysaccharides such as Sepharose®, or Sephadex®, both of which are available from Sigma-Aldrich; and acrylic copolymers, such as acrylamide/methylenebisacrylamide copolymers. Exemplary acrylic copolymer support materials include Sephacryl™ products available from Sigma Aldrich and BioGel P® polyacrylamide beads available from Bio-Rad.

A support phase can carry a stationary phase, as shown in FIG. 1. A stationary phase can in one preferred embodiment be in the form of an organic gel or liquid extraction resin that can include an organic solvent. An organic extraction resin can also include a compound, i.e., an extractant, which can affect the separation of uranium from the mobile phase contacting the support phase, with separation being based on chemical interactions between an extractant of the stationary phase and uranium carried in the aqueous mobile phase.

There are several extraction resins as may be utilized in disclosed systems that are capable of extracting uranium from an aqueous mobile phase. In one embodiment, an extraction resin incorporating a diamyl amylphosphonate (DAAP) extractant can be utilized. Exemplary extractant media including DAAP as extractant include U/TEVA and U/TEVA-2 extraction resins, available from Eichrom Technologies, Inc. The DAAP extractant forms nitrato complexes with actinide elements, including uranium. Other extraction media as may be utilized to extract uranium from a sample include dyglycolamide extractant materials as are described in U.S. Patent Application Publication No. 2004/0062695 to Horwitz, et al., which is incorporated herein by reference, Cyanex 923® extraction resin, bis-(2-ethylhexyl)phosphoric acid (HDEHP) (LN resin), 2-ethylhexyl 2-ethylhexylphosphonic acid (HEH[EHP]) (LN2 resin), and bis-(2,4,4trimethylpentyl) phosphinic acid (H[TMPeP]) (LN3 resin).

In the embodiment illustrated in FIG. 1, the extractant resin is impregnated within the pores of the stationary phase. Any arrangement of the stationary phase and the support phase can be utilized such that the aqueous mobile phase can contact the stationary phase and uranium can be extracted from the aqueous phase by the extractant of the stationary phase. For example, the extractant resin can form a continuous or discontinuous coating on the surface of a non-porous support phase, the extractant resin can be located within channels or other open voids defined by a support phase, and so forth.

A liquid-liquid extraction process can be carried out to form a concentrated uranium sample. According to this process, a support phase is not required and the extraction media is not necessarily in the form of a stationary phase. Rather, according to a liquid-liquid extraction method, an extractant can be a component of a liquid extraction medium that includes an organic solvent. An aqueous sample can then be mixed with the organic extraction media to bring the extractant and the uranium in association distance of one another and encourage chemical interaction between the two. Following mixing, the organic and aqueous phases can be allowed to separate, with the uranium now held in the organic phase by the extractant dissolved therein. In general, similar extractants can be utilized in a liquid-liquid extraction process as are utilized in solvent-based extraction chromatography process. For instance, an organic solution of diamyl amylphosphonate (DAAP) extractant, dyglycolamide extractant, bis-(2-ethylhexyl) phosphoric acid (HDEHP), 2-ethylhexyl 2-ethylhexylphosphonic acid (HEH[EHP]), or bis-(2,4,4trimethylpentyl) phosphinic acid (H[TMPeP]), can be utilized in a liquid-liquid extraction process.

In another embodiment, a solid phase extraction process can be carried out. According to this embodiment, an extractant, e.g., a ligand that binds uranium, can be immobilized directly onto the support phase of a system, e.g., within the pores and/or on the surface of a support phase. For instance, tricarboxylic and trishydroxamic calix[6]arenes can be utilized as a stationary phase ligand for the concentration of uranium. Solid phase extraction columns incorporating such extractants are available from Institut de Radioprotection et de Sûreté Nucléaire DRPH/SDI/LRC BP 17; 92262 Fontenay aux Roses Cedex; France. Another stationary phase extractant as can be utilized in disclosed systems is Superlig®191, available from IBC Advanced Technologies, Inc. of American Fork, Utah.

In yet another embodiment, an ion exchange process can be carried out so as to extract uranium from an aqueous test sample. Ion exchange can be preferred in one embodiment, as it can provide a facile method of extracting uranium from a sample without extracting other materials that can interfere with detection of the uranium. For instance, traces of most metallic elements in large volumes of natural waters can pass through an anion exchange column, while uranium can be concentrated on the column. By way of example, Dowex™ 21K is a strong-base anion exchange resin with trimethylamine functional groups that can be effective in removing more that about 90% of the uranium from a neutral, low-nitrate containing groundwater. This resin is ineffective, however in removing uranium from high-nitrate containing groundwater.

In one embodiment, a concentration method can preferentially remove uranium from a test sample while leaving other metals, and in particular metals that can interfere with detection regimes. However, separation materials, e.g., extractant, ion exchange resins, etc., as may be utilized herein are not limited to those that can exclusively separate uranium to the exclusion of all other potentially interfering metals from an aqueous sample. In particular, it should be understood that suitable separation materials encompass those that can remove uranium as well as other metals from an aqueous phase, including other metals that can potentially interfere with detection/quantification of uranium in the sample. For instance, in addition to uranium, cadmium, copper, iron, manganese, and zinc can all be extracted from a water sample by the extractant media U/TEVA-2.

There are several processes for preventing interference of such materials in the disclosed detection regimes, any of which can be included in disclosed methods. In one embodiment, a sample can be pre-treated so as to prevent separation from an aqueous sample of an interfering metal in conjunction with uranium. For example, iron will only be retained by U/TEVA resin in the +3 state. Accordingly, adding a suitable treatment reagent to a sample, such as ascorbic acid, can reduce iron in the sample to +2, causing it to be eluted from the column rather than retained in the stationary phase. Similarly, aluminum nitrate added to a sample can prevent the extraction of phosphate onto a U/TEVA resin, and thus can be utilized as a treatment reagent to prevent the interference of phosphate.

In another embodiment, following extraction of multiple metals, a treatment reagent can be utilized as an eluent to remove interfering metals from a column, while leaving the uranium on the column. For instance, nitric acid can be utilized to elute several different metals, including cadmium, copper, iron, magnesium, and nickel, from a stationary phase of an extraction column, but will not similarly remove uranium from the stationary phase. In another embodiment, elements such as iron and plutonium can be eluted from a solvent phase extraction column with a 9:1 solution of 8 N HCl to 47% HI. This solution does not, however, elute uranium on the column. According to such an embodiment, following elution of the other materials, uranium can be eluted separately to form a concentrated uranium sample.

Disclosed methods can also be utilized in combination with known masking methodology. More specifically, materials that can be extracted in conjunction with uranium can be masked by use of a treatment reagent, either prior to extraction or following elution, so as to avoid interference during uranium detection. For example, U.S. Pat. No. 6,107,098 to Kalinich, which is incorporated herein by reference, describes compounds including a combination of EDTA and sodium citrate that can be utilized to mask from detection certain elements that can be carried with uranium during concentration steps. A masking compound as described by Kalinich can be combined with a sample either prior to or following an extraction/concentration regime. Following capture of uranium from a test sample by use of an extractant, the uranium can be separated from the extractant by use of a separation agent to form a concentrated uranium solution. For example, when utilizing an extraction column, uranium can be eluted from the column by use of a suitable eluent to form a concentrated uranium solution. Suitable separation agents can include, without limitation, a sodium carbonate solution, sodium bicarbonate solution or a nitric acid solution, with a preferred separation agents generally depending upon the specific system type and extractant used. For instance, a solvent-based extraction chromatographic system can utilize a sodium carbonate or sodium bicarbonate eluent, and a solid-phase system can utilize a nitric acid solution eluent. In general, uranium can be effectively separated from an extractant with any separation agent that can form a stronger complex with uranium than does the extractant, e.g., the formation of the separation agent/uranium complex is more favorable chemically than is the formation of the extractant/uranium complex. For instance, sodium carbonate or sodium bicarbonate eluent can be preferred to remove uranium from an extraction chromatographic column, as these compounds can remove uranium from the column while leaving other potentially interfering metals behind.

Depending upon the specific characteristics of a system, additional steps may be taken to improve the extraction and concentration of uranium from a test sample. For instance, when utilizing a 0.1 M $Na_2CO_3$ eluent solution, uranium retention rises at higher pH when utilizing LN3 resin, while the opposite is true for U-TEVA2 resin, i.e., uranium retention falls for U-TEVA2 resin at higher pH. This indicates that pH adjustment of the eluent can be utilized to prevent uranium breakthrough. For example, when utilizing a U-TEVA2 resin, samples can be acidified by use of a suitable treatment reagent to at least about pH 3 prior to the concentration step.

In order to carry out a detection step, uranium can be complexed with a detectable substance, either prior to, during, or following the concentration of the uranium. For instance, following elution of uranium from an extraction column, the uranium of the concentrated solution can be complexed with a detectable substance. According to one embodiment, a detectable substance can form a visibly detectable soluble aqueous chelate with uranium. For instance, a pyridylazo indicator dye can be utilized. Exemplary pyridylazo indicators capable of forming a complex with uranium to provide a visibly detectable complex include 2-(5-bromo-2-pyridylazo)-5-diethylaminophenol (Br-PADAP) and 1-(2-pyridylazo)-2-naphthol. Other uranium complexing materials as may be utilized include glyoxal bis (2-hydroxy-anil), Arsenazo III, and so forth. The complex formed between the uranium and the detectable substance can be visually detectable.

Beneficially, due to the concentrating step of disclosed methods, even when uranium is present in the original sample at very low levels, for instance levels near the MCL as established by the EPA, the complex including uranium and the detectable substance can be visually detectable. As such, disclosed methods can be carried out without the need for expensive laboratory equipment, such as spectroscopes and the like. Moreover, in one preferred embodiment, visual indication of uranium in a sample can vary with regard to color depending upon the concentration of uranium in the sample. Thus, a calibration curve can be formed that can establish the correlation between uranium concentration and visual response of the system to provide a user with quantitative information with regard to the uranium contamination of a water sample.

As previously mentioned, disclosed methods can encompass steps in addition to the concentration and detection steps. For instance, in an embodiment in which sodium carbonate or sodium bicarbonate is utilized as an eluent to remove uranium from the stationary phase and Br-PADAP is utilized as the indicator agent, it can be beneficial to include an additional step in the process to break uranyl carbonate complex that can be formed during a concentration step, as the uranyl ion, $UO_2^{+2}$, forms a complex with carbonate, $CO_3^{-2}$, and this complex is understood to be stronger than a complex formed between $UO_2^{+2}$ and Br-PADAP. However, Br-PADAP can complex with uranium in the form of uranyl nitrate as the uranyl nitrate complex is a weaker complex than that between $UO_2^{+2}$ and Br-PADAP. Thus, when sodium carbonate is used as the eluent, and column effluent is in the form of uranyl carbonate, the bond between $UO_2^{+2}$ and $CO_3^{-2}$ can be broken and uranyl nitrate can be alternatively formed, prior to formation of the detectable complex. Upon addition of Br-PADAP to the concentrated uranyl nitrate solution, a visibly detectable Br-PADAP complex can be formed.

Any suitable strategy can be utilized to break a uranyl carbonate complex. In one embodiment, a concentrated uranyl carbonate sample can be boiled rigorously to convert remaining carbonate to $CO_2$ and release the $CO_2$. In yet another embodiment, extraction chromatography can be followed with ion chromatography, so as to replace a carbonate ion with an ion that weakly complexes to uranium, for instance $F^-$, $Cl^-$, or $OH^-$ ion exchange can be carried out. In another embodiment, solutions can be buffered to a lower pH.

The pH of the concentrated uranium solution can also effect the formation of the uranium/indicator complex. For instance, an unstable 1:1 Br-PADAP:uranium complex can be formed at neutral pH. When Br-PADAP is complexed with uranium, it becomes negatively charged due to loss of the hydroxyl proton. Because the uranyl ion has two positive charges, at neutral pH an additional −1 anion can be present to stabilize the complex. Thus, in one embodiment, a counterion can be provided to stabilize the uranium/indicator complex. A counterion can be provided by the addition to the concentrated uranium sample of, for example, NaF, NaCl, and so forth.

Disclosed methods can be utilized to quickly and easily determine information with regard to uranium presence in an aqueous sample. Beneficially, disclosed methods can be utilized in one preferred embodiment without the need of expensive laboratory techniques or devices.

Figure 2:
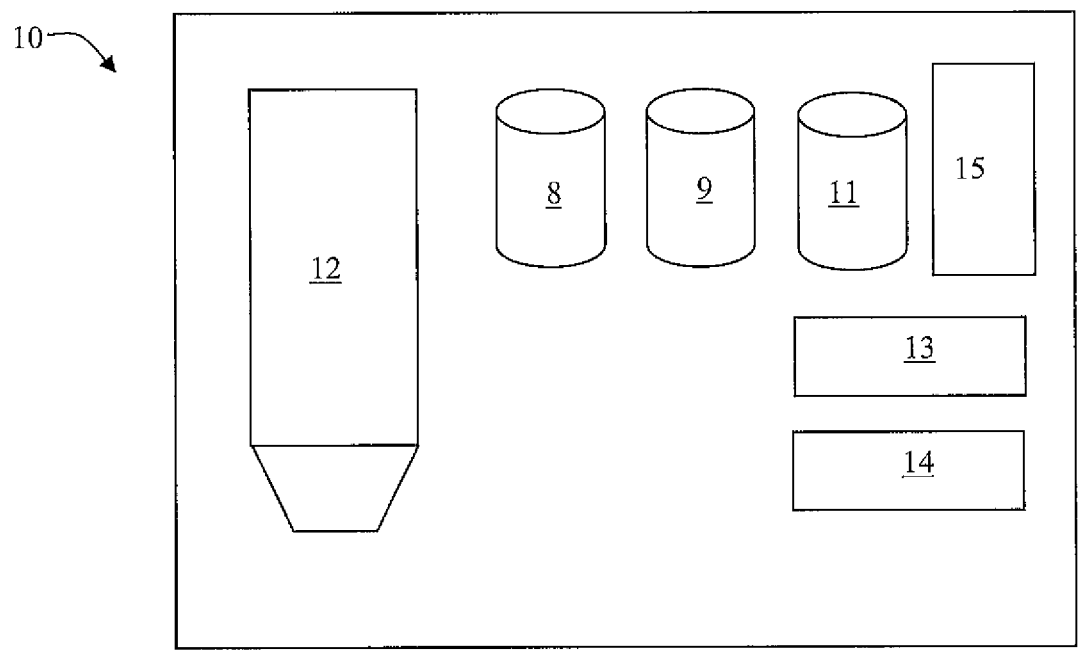
FIG. 2 is a schematic representation of one embodiment of a portable test system as disclosed herein.

According to one such embodiment, illustrated in FIG. 2 is a schematic representation of a convenient, portable system 10 that can be used to determining the presence or quantity of uranium in an aqueous test sample. For instance, a portable system 10 can be sold as a portable kit for use by home owners, field workers, or others, to determine information with regard to uranium presence or quantity in an aqueous test sample. An aqueous test sample can be a sample including natural waters, in one embodiment. In general, the term 'natural waters' as used herein encompasses both groundwater and surface water. According to one preferred embodiment, a test sample can include drinking water. For instance, drinking water formed of treated or untreated groundwater, treated surface water, or the like, can be conveniently tested according to disclosed methods.

As can be seen, a system 10 can include various elements including a uranium concentrator 12. A concentrator 12 can include an extractant for binding uranium in an aqueous sample, as described above. For instance, a concentrator can be an extraction chromatographic column containing a support phase, such as a plurality of porous beads impregnated with a stationary phase comprising an extractant as illustrated in FIG. 1. Any suitable concentrator can be incorporated into system 10, however, and a portable system is in no way limited to an extraction chromatographic type concentrator. For example, in another embodiment, a concentrator can encompass a mixing container including a liquid extractant medium, for instance when carrying out a liquid-liquid extraction process.

A system 10 can also include detectable substance 14. In general, a detectable substance 14 can be contained in a sealed vessel prior to utilization. For instance, following extraction of uranium from a sample on an extraction column and elution of the uranium from the column to form a concentrated uranium sample, the sealed vessel containing a detectable substance 14 can be opened and the detectable substance can be combined with the concentrated uranium sample.

A system can also include a variety of containers and testing reagents for use during a test. For instance, a system 10 can include a sample container 8 that can include appropriate markings to provide a predetermined quantity of a test sample to concentrator 12. A system 10 can also include a series of receiving containers 9, 11 for receiving a liquid flow as it exits a concentrator 12. For example, a first receiving container 9 can receive a liquid flow off of the bottom of the concentrator 12 after the test sample has been poured in to the top of the concentrator 12. Hence, this liquid flow can contain that portion of the test sample not extracted by the extractant as the test sample passes through the concentrator 12.

Following, a separation agent held in a sealed vessel 13 can be added to the top of the concentrator. The separation agent can separate the extracted materials, including any uranium from the test sample, and this flow can be collected in a second receiving container 11, to form a concentrated uranium sample that can then be combined with the detectable substance.

A portable system 10 can contain other components as desired such as printed calibration data 15 that can display information with regard to one or more of color, hue, brightness, etc. of the visibly detectable substance and related uranium concentration of the test sample. Other components can include treatment reagents, e.g., pH modifiers, eluents for removal of potentially interfering compounds from a non-specific extractant, masking compounds, and the like, as well as useful materials such as litmus paper, and so forth.

A system can include a second concentration device. For instance, a system can include an ion exchange column that can be utilized to separate uranium from the separation agent used in the concentrator, or an exchange column to separate uranium of the concentrated sample from other potentially interfering compounds. Other variations and additions to a portable system 10 are encompassed herein as would be apparent to one of ordinary skill in the art.

The present disclosure may be further understood with reference to the Examples, set forth below.

EXAMPLES

Reagents and Apparatus

Granular, anhydrous sodium carbonate, ACS grade, was purchased from Mallinckrodt. 2-(5-bromo-2-pyridylazo)-5-diethylaminophenol (Br-PADAP, 97%) was purchased from Sigma-Aldrich. Reagent alcohol (94-96% ethanol+methanol, 4-6% isopropyl alcohol) was purchased from BDH. Sodium fluoride, USP grade, was purchased from EM Science, Nitric acid (1.000±0.005 N) was purchased from VWR. Triethanolamine hydrochloride (TEA) was purchased from Acros Organics. Sodium hydroxide (1.00 N ACS/APHA/EPA/USP volumetric solution) and the uranium reference standard (1000 µg) were purchased from Ricca Chemical Company. Pyridine (High Purity Solvent) was purchased from Burdick & Jackson. Perchloric acid (OmniTrace) was purchased from EMD. Sodium borate (10-Hydrate Crystal Baker Analyzed Reagnet) was purchased from J. T. Baker, Inc. All reagents were used as received.

A Thermo Orion model 420A+pH meter equipped with a VWR sympHony electrode was used to obtain all pH measurements. Before use, the meter was calibrated with three pH standard solutions: pH 7.00, pH 4.01, and pH 10.01. The meter was used when a slope of 98.0 or greater was obtained. The electrode was rinsed with deionized water between each measurement and stored in deionized water when not in use.

UV-Visible spectrophotometric analyses were carried out on a Varian Cary 300 Bio UV-Visible Spectrophotometer. The instrument was zeroed with deionized water and all samples were analyzed from 350 nm to 700 nm.

Solution Preparation

Sodium carbonate was prepared in deionized water from solid $Na_2CO_3$ to yield a 0.01 M solution. Br-PADAP solutions were prepared in 50% (v/v) reagent alcohol from approximately 0.0003 g solid Br-PADAP to yield a $10^{-5}$ M orange solution. Sodium fluoride was prepared in deionized water from approximately 0.08 g solid NaF to yield a 0.02 M solution. TEA buffer was prepared in deionized water from approximately 18.5 g solid triethanolamine hydrochloride to yield a 1 M solution, which was titrated to pH 7.30 with 1 N NaOH. Pyridine buffer was prepared in deionized water from 8 mL pyridine to yield a 1 M solution, which was titrated to pH 4.10 with perchloric acid. Borate buffer was prepared from $Na_2B_4O_7.10H_2O$ and deionized water to yield a 25 or 50 mM solution, which was titrated to pH 10.00 with 1 N NaOH. Uranium solutions were prepared by diluting the uranium reference standard with deionized water.

Sample Collection

Six groundwater samples were collected from private wells known to have high uranium concentrations. Before water collection at the well heads, water was flushed until a constant conductivity reading was measured to ensure access to fresh well water. For example, approximately 4 L of water was collected from a campsite faucet located within Devil's Fork (S.C.) State Park (N 34° 57'25.4", W 82° 57'6.0"). Water was allowed to run from the faucet until constant water temperature and conductivity were reached. Water was collected in 1 L bottles without headspace and acidified to pH 2 with 8 M $HNO_3$.

Samples were acidified to pH 2 and aerated for 15 minutes to remove dissolved $^{222}Rn$. Samples were stored at 4° C. Additional methodology of sample collection is further described by Hughes, et al., "Anomalously High Levels of Uranium and Other Naturally Occurring Radionuclides in Private Wells in the Piedmont Region of South Carolina," Health Physics, Vol. 88, No. 3, 248-252 (2005). Uranium concentration was determined by alpha spectroscopy.

Example

To determine the percent recovery of uranium from different resins (LN3 or U/TEVA-2), solutions containing a known amount of uranium were drawn through columns under vacuum with an estimated initial flow rate of 2 mL/min. Fractions were collected when water samples were first passed through U/TEVA-2 or LN3 columns. These fractions were analyzed by gamma spectroscopy to determine uranium-235 breakthrough.

Gamma spectroscopy analysis was based on the 185.71 keV gamma ray for $^{235}U$. The $^{235}U$ (57.20% emission fraction) spike had a concentration of $3.15 \times 10^{-5}$ µCi/mL. Because of a software artifact, the $^{235}U$ activity in the loading and uranium effluent gamma vials was calculated by multiplying the $^{226}Ra$ activity (µCi) by the ratio of the $^{226}Ra$ emission fraction to the $^{235}U$ emission fraction. The percent uranium recovery was then calculated with equation 1, below, where the activity loaded onto the column is equal to $1.82 \times 10^{-4}$ µCi and $1.82 \times 10^{-6}$ µCi at pH 3 and 4, respectively.

$$Recovery(\%) = \frac{\text{Activity Eluted from Column}}{\text{Activity Loaded onto Column}} \times 100\% \quad (1)$$

Loading effluents were collected in 40 mL increments at a flow rate of approximately 2 mL/min. Uranium was eluted with a given volume and concentration of sodium carbonate, which was collected in a separate vial. Gamma vials (three milliliter aliquots) were prepared from the original solutions, each loading effluent fraction, and the uranium elution, and analyzed by gamma spectroscopy.

Specifically, for gamma spectroscopy, all loading effluent fractions from both LN3 and U/TEVA-2 as well as the uranium-235 spike solution were counted for one hour on one of two Ortec P-type HPGe GEM detector outfitted with a Changer Labs automated gamma sample changer, 4 inch graded lead shield and Can berra Genie 2000 gamma spectroscopy software. Relative counting efficiencies were 35 and 40%. Most sodium carbonate effluents were also counted for one hour. However, select samples were analyzed for 8 hours. One sample was analyzed for 14 hours on an Ortec P-type HPGe GEM detector equipped with a Gamma Products model G11-E 4 inch graded lead shield. This detector had a 30% relative counting efficiency. All detector systems were situated in a low-level counting room shielded with an additional 2 feet of concrete.

Figure 3:
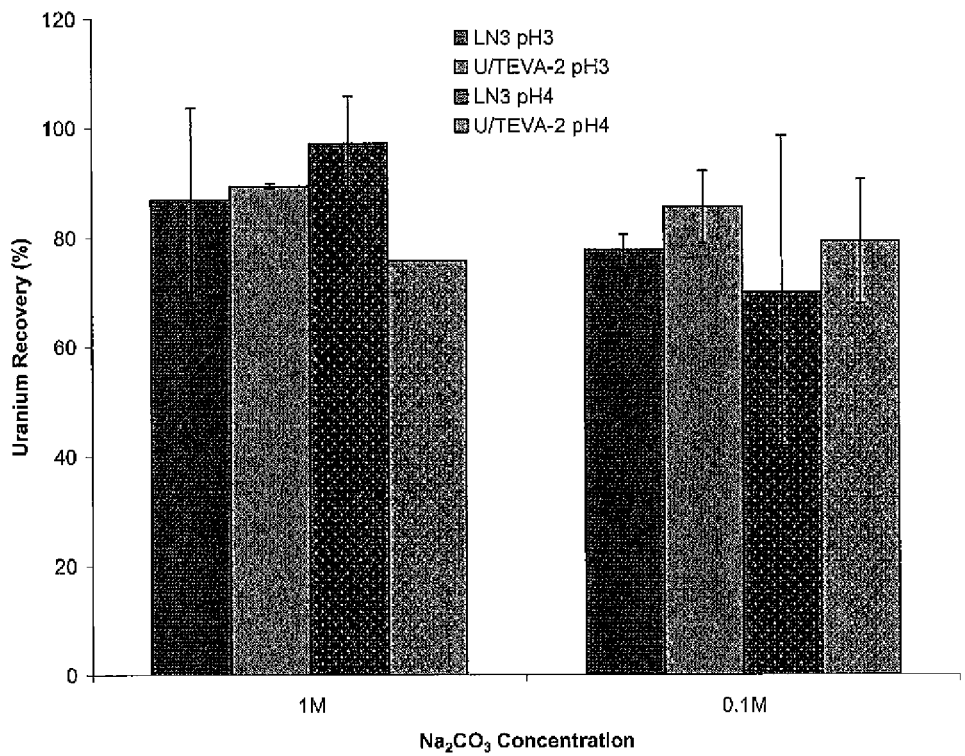
FIG. 3 compares the percent uranium recovery from LN3 and U/TEVA-2 resins as a function of sample pH and eluent concentration.

No uranium was detected above the minimum detection activity of approximately $10^{-6}$ µCi/mL for a one hour count time, indicating that the greatest amount of uranium breakthrough could have been $6\times10^{-6}$ µCi/mL, which is 3% of the activity loaded onto the column. Therefore, incomplete recovery may indicate there is some uranium remaining on the column. Uranium may have bound irreversibly to the column support or stationary phase, sodium carbonate may have been passed through the column faster than equilibrium could be established, or insufficient amounts of sodium carbonate may have been present to strip all uranium. FIG. 3 compares the percent recovery of uranium on LN3 and U/TEVA-2 columns at two different sodium carbonate eluent concentrations, 1 M and 0.1 M, and two different pH values of the load solution, 3 and 4.

Alpha spectroscopy was carried out on an EG&G Ortec Alpha Spectroscopy System equipped with Octete PC alpha spectrometers. Detector efficiency was determined by counting a 7511_Bq $^{241}$Am source for 300 s. Planchets were prepared by evaporating sample aliquots to dryness and holding in a Bunsen burner flame until glowing red. All samples were analyzed for at least 13 hours with detector efficiencies ranging from 4-7%. Two planchets were prepared as a quality assurance/quality control measure (QA/QC). One contained deionized water spiked with 1 N $HNO_3$ and the other contained 0.01 M $Na_2CO_3$. No activity was detected from these samples.

For alpha spectroscopy, the activity (Bq) eluted from the column was calculated by subtracting the background count rate from the sample count rate and dividing by the detector efficiency. The activity loaded onto the column was equal to 0.31 Bq.

As can be seen with reference to FIG. 3, for the pH 3 load solution, 1 M $Na_2CO_3$ elutes approximately 90% uranium from U/TEVA-2 and an average of 87% uranium from LN3. For the pH 4 load solution, the percent recovery of uranium is significantly less for U/TEVA-2, only 75%. However, the average recovery from LN3 increased to 97%.

Due to the strong affinity of the uranyl ion, $UO_2^{+2}$, for carbonate, it is more desirable to use the lowest possible concentration of sodium carbonate to strip uranium from the columns. From FIG. 3, it is apparent that, on average, lower sodium carbonate concentrations elute less uranium from both U/TEVA-2 and LN3 resins. While 1 M $Na_2CO_3$ was able to elute an average of 87% uranium from LN3 than was loaded at pH 3, 0.1 M $Na_2CO_3$ only eluted an average of 78% uranium. Although there is greater variability in the amount of uranium eluted from LN3 with a pH 4 load solution using 0.1 M $Na_2CO_3$ than at 1 M $Na_2CO_3$, complete recovery of uranium is believed to be possible under both conditions if volumes greater than 10 mL are used. At 0.1 M $Na_2CO_3$, an average of 85% and 80% uranium was eluted from U/TEVA-2 columns at pH 3 and pH 4 loading conditions, respectively. A maximum of approximately 90% uranium could be eluted at either pH. As such, all samples were acidified to pH 2 for the remainder of method development.

Uranium in Groundwater Tests

The same procedure as described above was utilized using groundwater samples collected from private wells. With the exception of sample no. 6, which was performed in triplicate, all experiments were performed in duplicate. Table 1 shows the volumes of well water samples used to load 7.6 to 140.2 µg uranium onto each U/TEVA-2 column. At least 1 L of sample could be concentrated with a U/TEVA-2 column without breakthrough. Therefore, the last column of Table 1 effectively represents uranium concentrations of 7.6 µg/L to 140.2 µg/L.

TABLE 1

| Sample ID | Sample Uranium Concentration (µg/L) | Sample Volume (mL) | Uranium Loaded onto Columns (µg) |
|---|---|---|---|
| 1 | 76.0 ± 0.2 | 100 | 7.6 |
| 2 | 20.9 ± 0.1 | 1000 | 20.9 |
| 3 | 317.3 ± 0.8 | 80 | 25.4 |
| 4 | 317.3 ± 0.8 | 105 | 33.3 |
| 5 | 78.8 ± 0.2 | 1000 | 78.8 |
| 6 | 1402.1 ± 3.7 | 100 | 140.2 |

To insure there was no uranium breakthrough when using groundwater samples, all loading effluent was evaporated to dryness and re-dissolved in 1 N $HNO_3$. Aliquots of this solution were analyzed by alpha spectroscopy where no activity was determined.

Example 2

To investigate the ability of U/TEVA-2 to eliminate metal interferences, 2 mL of a metal containing 1000 ppm emission spectrometry (ES) standard solution was combined with 1 mL 1 N $HNO_3$ and evaporated to dryness. The residue was re-dissolved in 20 mL of 0.1 N $HNO_3$. Ten milliliters of this solution were diluted in 30 mL deionized water, which was then passed through a U/TEVA-2 column under vacuum. This loading effluent was discarded and the column was eluted with 10 mL of 0.1 M $Na_2CO_3$. This was completed in duplicate. Sodium carbonate effluents were then analyzed by inductively coupled plasma emission spectrometry (ICP-ES Leeman Prodigy ICP-ES model 6048 with a method uncertainty of ±10%). Table 2 shows the metals contained in the ES standard solution, each at 1000 ppm. Reported % RSD values reflect the variance in replicate measurements of the same sample. This error was propagated when calculating the average of the two sodium carbonate effluents.

TABLE 2

| Metals Included in 1000 ppm Solution | | |
|---|---|---|
| Aluminum | Barium | Calcium |
| Cerium | Chromium | Iron |
| Gadolinium | Potassium | Lanthanum |
| Lithium | Magnesium | Manganese |
| Sodium | Nickel | Lead |

Table 3 displays the metals that were detected. Barium, calcium, chromium, iron, lanthanum, lithium, magnesium, manganese, and sodium were all components of the metal standard that was passed through the column. The large excess of sodium is also due to the 0.1 M $Na_2CO_3$ used to strip the metals from the column. The presence of phosphorus results from elution of the chemical extractant from the column and the other elements—boron, cadmium, copper, strontium, vanadium, and zinc—likely result from impurities in sodium carbonate or nitric acid.

TABLE 3

| Element | Avg. Concentration (mg/L) | Fraction Removed |
| --- | --- | --- |
| B | 2.83 ± 9.98% | 0.972 |
| Ba | 1.99 ± 4.55% | 0.980 |
| Ca | 2.67 ± 6.41% | 0.973 |
| Cd | 1.68 ± 9.44% | 0.983 |
| Cr | 35 ± 1.53% | 0.650 |
| Cu | 1.49 ± 7.03% | 0.985 |
| Fe | 7.31 ± 1.99% | 0.927 |
| La | 1.89 ± 12.63% | 0.981 |
| Li | 2.39 ± 7.18% | 0.976 |
| Mg | 2.15 ± 0.73% | 0.979 |
| Mn | 1.09 ± 6.56% | 0.989 |
| Na | 4530 ± 0.21% | n/a |
| P | 19 ± 10.08% | 0.810 |
| Sr | 2 ± 0.51% | 0.980 |
| V | 29.85 ± 0.58% | 0.702 |
| Zn | 1.94 ± 4.58% | 0.981 |

Generally, the U/TEVA-2 column removed more than 97% of the metals in the load solution.

Example 3

Experiments were prepared to investigate the effect of Br-PADAP concentration on complex formation. Four Br-PADAP concentrations were used: $10^{-6}$, $5 \times 10^{-6}$, $10^{-6}$, and $10^{-4}$ M. Triethanolamine was used to buffer solutions to pH ~7.3. The counterion was provided by the addition of 0.02 M NaF. With the exception of $10^{-6}$ M Br-PADAP, all experiments were performed in triplicate. For all four Br-PADAP concentrations, an attempt was made to produce a calibration curve with uranium concentrations spanning five orders of magnitude: $10^{-8}$, $10^{-7}$, $10^{-6}$, $10^{-5}$, $10^{-4}$, and $4 \times 10^{-3}$ M. Three milliliters of each uranium solution was used.

Samples prepared with $10^{-6}$ M Br-PADAP were very faint in color with no visual distinction between uranium concentrations from $10^{-8}$ to $4 \times 10^3$ M. Analyses of these samples by UV-Visible Spectrophotometry were poorly resolved. Samples at $5 \times 10^{-6}$ M Br-PADAP exhibited a color trend visible to the eye in the same uranium concentration range. Those containing less than $10^{-5}$ M uranium were yellow, $10^{-5}$ M uranium was pink, $10^{-4}$ M was purple, and $4 \times 10^3$ M was orange. However, the maximum absorbencies of these solutions were less than 0.08.

Figure 4:
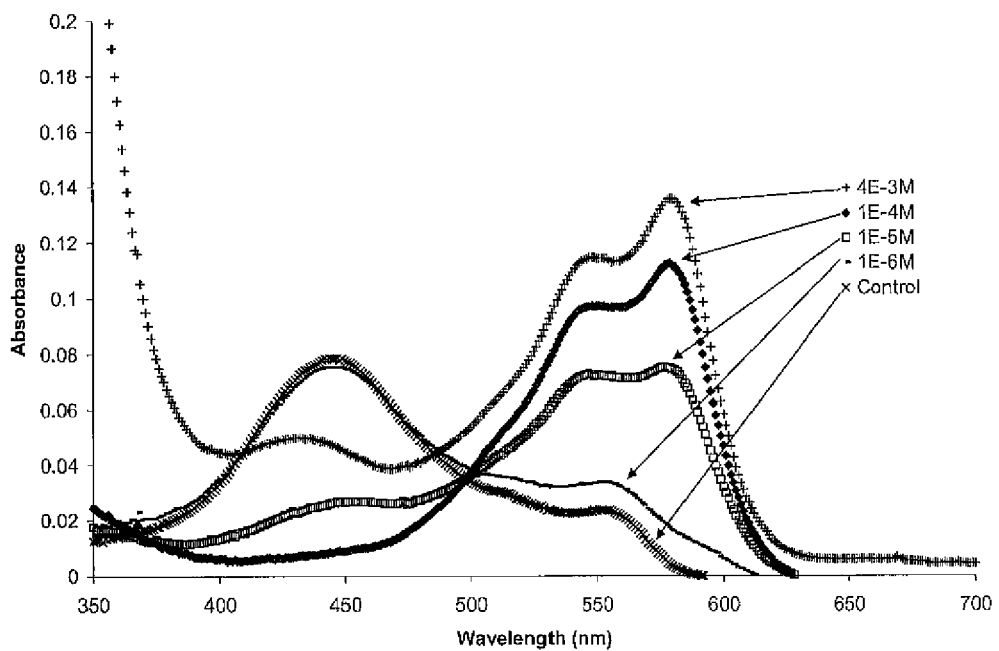
FIG. 4 illustrates the effect of uranium concentration on Br-PADAP:uranium complex formation at $10^{-5}$ M Br-PADAP, 1 M TEA, and 0.02 M NaF. The absorbance spectra were measured with a spectrophotometer.

Samples containing $10^{-5}$ and $10^{-4}$ M Br-PADAP had the most favorable results. FIG. 4 is a graph of absorbance versus wavelength for a range of uranium concentrations at $10^{-5}$ M Br-PADAP. The peak at 450 nm represents the free, or uncomplexed, Br-PADAP in solution. As would be expected, the absorbance at this wavelength decreases with increasing uranium concentration, corresponding to the formation of a Br-PADAP:uranium complex. The sudden increase and slight shift of the 450 nm peak to shorter wavelengths at the highest uranium concentration corresponds to the formation of uranyl nitrate, a yellow precipitate. The double peak at 550 and 578 nm represents the Br-PADAP:uranium complex and the absorbance at these wavelengths increases with increasing uranium concentration. Color change was visible to the naked eye. Uranium concentrations below $10^{-5}$ M were yellow; those at or above $10^{-5}$ M uranium were purple.

Figure 5A:
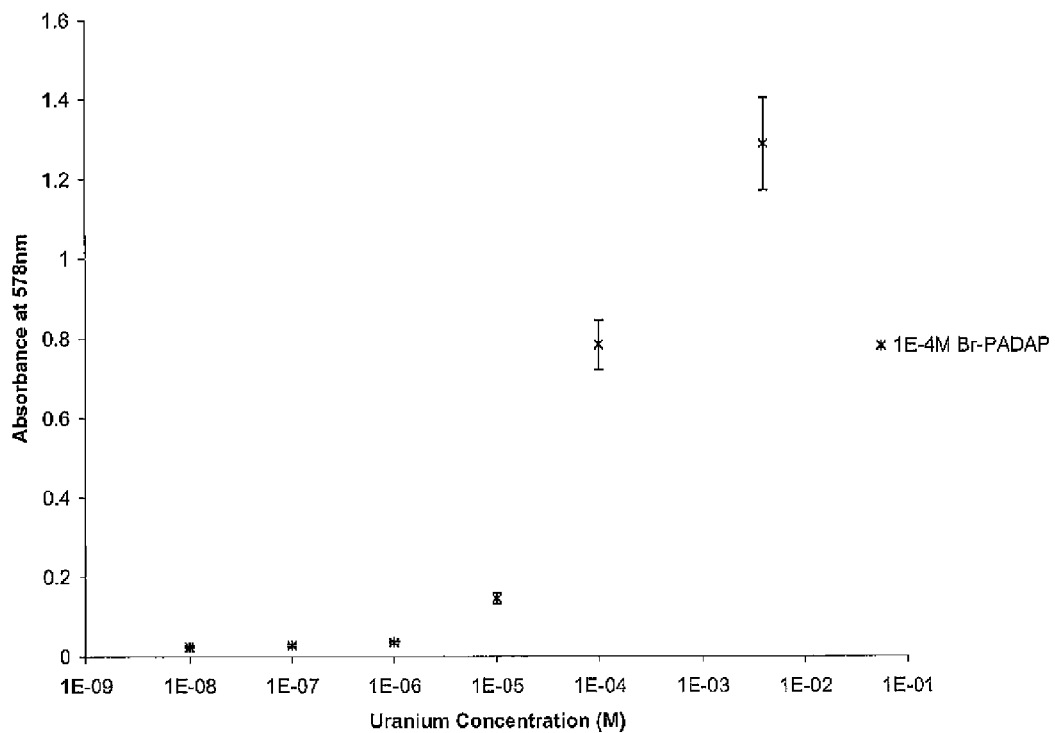
FIGS. 5A and 5B illustrate the correlation between uranium concentration and Br-PADAP:uranium complex absorption at four different Br-PADAP concentrations.
Figure 5B:
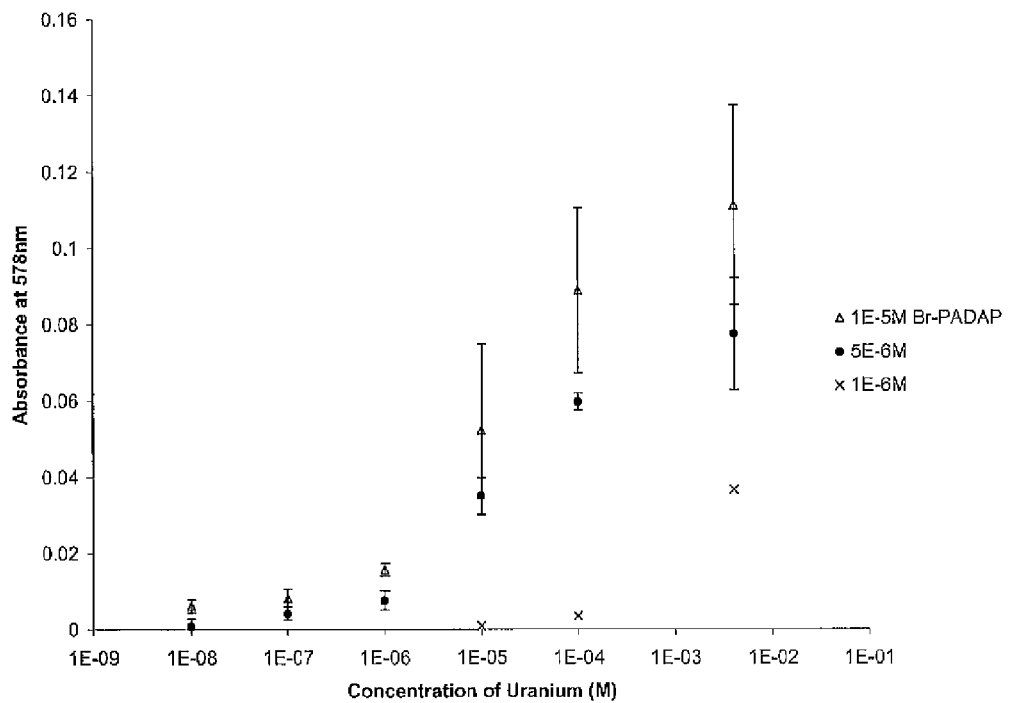

FIGS. 5A and 5B illustrate absorbance of the Br-PADAP:uranium complex as a function of uranium concentration, FIG. 5A displays data for $10^{-4}$ M uranium while FIG. 4B displays data from $10^{-6}$, $5 \times 10^6$, and $10^{-5}$ M Br-PADAP. For all four Br-PADAP concentrations, the trend reveals saturation behavior. At $5 \times 10^{-6}$ and $10^{-5}$ M Br-PADAP there is a clear linear trend from $10^{-6}$ to $10^{-4}$ M uranium; outside this region, the trend becomes nonlinear. There are no linear trends for $10^{-6}$ or $10^{-4}$ M Br-PADAP.

A graph of absorbance versus wavelength for $10^{-4}$ M Br-PADAP (not shown) is similar to that seen in FIG. 4 for $10^{-5}$ M Br-PADAP. There is a peak at 450 nm representing the uncomplexed Br-PADAP in solution. The absorbance at this wavelength decreases with increasing uranium concentration, corresponding to the formation of a Br-PADAP:uranium complex. There is also the characteristic double peak at 550 and 578 nm represents the Br-PADAP:uranium complex, which increases with increasing uranium concentration. At this higher Br-PADAP concentration, solutions containing uranium concentrations below $10^{-5}$ M are orange, the $10^{-5}$ M solution is yellow, and solutions above $10^{-5}$ M uranium are purple.

Table 4 summarizes the results from experiments performed at $10^{-5}$ M and $10^{-4}$ M Br-PADAP. Although both sets of experiments were successful and very similar spectrophotometrically, the color change visible to the eye distinguished them. The abrupt color change from $<10^{-5}$ M to $10^{-5}$ M uranium at $10^{-5}$ M Br-PADAP indicates a detection limit between $10^{-6}$ M and $10^{-5}$ M uranium. The sequence of color changes for $10^{-4}$ M Br-PADAP was much more gradual and indicated a higher detection limit between $10^{-5}$ and $10^{-4}$ M uranium.

TABLE 4

| [Br-PADAP] | $<10^{-5}$ M U | $10^{-5}$ M U | $>10^{-5}$ M U |
| --- | --- | --- | --- |
| $10^{-4}$ | orange | yellow | purple |
| $10^{-5}$ | yellow | purple | purple |

Example 4

A series of scoping experiments were performed to investigate the effect of pH on complex formation. Borate was used to buffer solutions to pH 10 and pyridine was used to buffer solutions to pH 4. NaF was utilized as counter ion in some cases, as indicated. For each buffer, there were four experiments: $10^{-4}$ M Br-PADAP with and without NaF and $10^{-5}$ M Br-PADAP with and without NaF (see Table 5, below).

The scoping tests involved preparing six solutions: three control vials containing 3 mL of deionized water and three vials containing 3 mL of $10^{-5}$ M uranium, which corresponds to the drinking water MCL (after preconcentration) established by the EPA. To all six solutions was added 3 mL of Br-PADAP, 2_mL of buffer, and in indicated runs, 2 mL of NaF.

Table 5 summarizes the eight scoping experiments. The success of an experiment was determined from analysis of UV-VIS spectra. Unsuccessful experiments were defined as having no indication of Br-PADAP:uranium complex formation. Mediocre experiments were defined as those exhibiting complex formation as a small shoulder on the peak representing uncomplexed Br-PADAP in solution. Successful experiments were defined as those with the characteristic double maxima (at $\lambda$=550 nm and 578 nm) for the Br-PADAP:uranium peak, which increased with increasing uranium concentration.

TABLE 5

| Experiment | [Br-PADAP] (M) | Buffer | NaF | Result |
|---|---|---|---|---|
| 1 | $10^{-4}$ | Borate | No | Mediocre |
| 2 | $10^{-4}$ | Borate | Yes | Mediocre |
| 3 | $10^{-5}$ | Borate | No | Successful |
| 4 | $10^{-5}$ | Borate | Yes | Successful |
| 5 | $10^{-4}$ | Pyridine | No | Unsuccessful |
| 6 | $10^{-4}$ | Pyridine | Yes | Mediocre |
| 7 | $10^{-5}$ | Pyridine | No | Successful |
| 8 | $10^{-5}$ | Pyridine | Yes | Unsuccessful |

Experiments 3 and 4 both involved $10^{-5}$ M Br-PADAP and borate buffer, without and with a counter ion, respectively. According to the results, in basic solutions, a neutral Br-PADAP:uranium complex is formed and no counter ion is needed to stabilize the complex. However, presence of a counter ion does not negatively affect complex formation.

Figure 6:
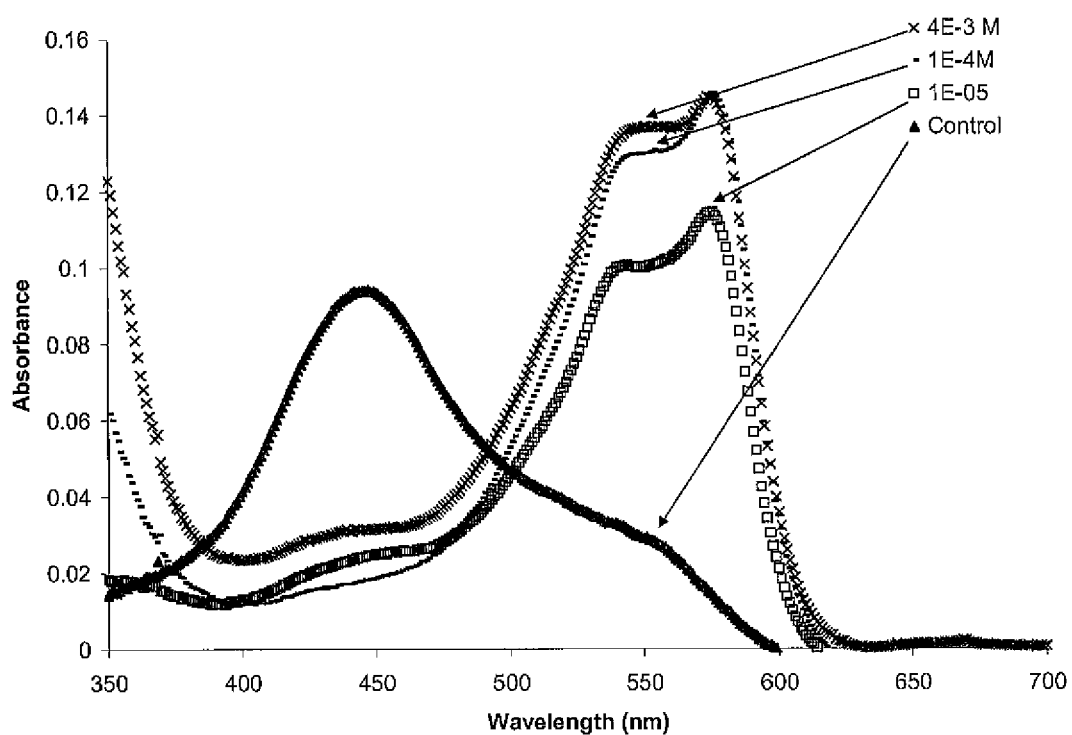
FIG. 6 illustrates the effect of uranium concentration on Br-PADAP:uranium complex formation at $10^{-5}$ M Br-PADAP and 25 mM Borate.

FIG. 6 is a graph of absorbance versus wavelength for a range of uranium concentrations at $10^{-5}$ M Br-PADAP and 25 mM borate. As before, the peak at 450 nm represents the uncomplexed Br-PADAP in solution. The absorbance at this wavelength decreases with increasing uranium concentration, corresponding to the formation of a Br-PADAP:uranium complex. The double peak at 550 and 578 nm represents the Br-PADAP:uranium complex and the absorbance at these wavelengths increases with increasing uranium concentration.

Example 5

A 1 L sample was acidified to pH 2 and passed through a U/TEVA-2 column under vacuum. The effluent was discarded. Uranium was eluted from the column with 20 mL 0.01 M $Na_2CO_3$, In order to break the carbonate and form uranyl nitrate, samples were boiled down to 3 mL after the addition of a small amount, 250 µL, of concentrated nitric acid, and the samples were then evaporated to dryness over medium heat. The residue was reconstituted in 3 mL 1 N $HNO_3$ and combined with 3 mL $10^{-5}$ M Br-PADAP, 2 mL 1 M TEA buffer, 2 mL NaF, and 400 µL 11.1 M $NH_4OH$. The sample sat for two hours to allow for color development. Uranium concentrations resulting in a purple solution were considered positive tests. Any other color (i.e. yellow or pink) indicated that the original solution had a uranium concentration below the method detection limit; this was, therefore, considered a negative test.

The UV-VIS spectra revealed shifts and deformation of the peak representing the Br-PADAP:uranium complex. This was hypothesized to be the result of excess sodium in solution resulting from sodium carbonate and sodium hydroxide. To test this hypothesis, samples were prepared in 0.01 M sodium carbonate and pH adjusted with ammonium hydroxide. Control samples were yellow and uranium solutions were purple. The double peak representing the Br-PADAP:uranium complex in the uranium solutions was no longer deformed.

The complete colorimetric procedure for quantification of uranium in groundwater is outlined below:
Acidify 1 L of sample to pH 2 with nitric acid Pass acidified sample through U/TEVA-2 column and discard effluent
Elute uranium with 20 mL 0.01 M $Na_2CO_3$
Add 240 µL concentrated $HNO_3$ to effluent and evaporate to dryness over medium heat
Dissolve residue in 3 mL 1 N $HNO_3$
Add 3 mL $10^{-5}$ M Br-PADAP, 2 mL 1 M TEA buffer, 2 mL 0.02 M NaF, and 400 µL 11.1 M $NH_4OH$
Develop sample for two hours and compare to color chart This method was tested using groundwater samples collected from a local area as described above. Table 6 summarizes the results of concentrating 7.6-140.2 µg uranium with the U/TEVA-2 columns. Based on the colorimetric detection limit of 2,14-7.14 µg/L uranium, it was expected that the 615JB and DFSP samples would be purple and return a positive result. The fact that these two samples were pink indicates a higher detection limit for the overall method between 20.9 µg/L and 25.4 µg/L. The discrepancy between the colorimetric and overall detection limits is hypothesized to be due to incomplete recovery or breakthrough of uranium in the groundwater samples during the concentration step.

TABLE 6

| Sample ID | Sample U concentration (µg/L) | Sample Volume (mL) | Uranium (µg) | Color | Result |
|---|---|---|---|---|---|
| 615JB | 76.0 | 100 | 7.6 | Pink | Negative |
| DFSP | 20.9 | 1000 | 20.9 | Pink | Negative |
| 210RW | 317.3 | 80 | 25.4 | Purple | Positive |
| 210RW | 317.3 | 105 | 33.3 | Purple | Positive |
| 158WWA4 | 78.8 | 1000 | 78.8 | Purple | Positive |
| 158WW | 1402.1 | 100 | 140.2 | Purple w/ ppt | Positive |

Example 6

To gain further understanding of the impact metal interferences have on a two-step method as outlined in Example 4, several of the groundwater samples were subjected to the same colorimetric process except no concentration/uranium purification step was performed. Table 7 summarizes the results of these experiments. The expected color for each solution is based on the colorimetric detection limit of 2.14-7.14 µg/L uranium. Solutions containing uranium concentrations below this detection limit should have been yellow, those within the detection limit should have been gray, and those above the detection limit should have been purple. The discrepancy between the observed and expected colors for the first two samples indicated higher concentrations of uranium in those samples. These results indicate that in the case in which metals other than uranium are present in the sample, these other metals can be complexed with the Br-PADAP. These results further support the use of a concentration step such as extraction chromatography to eliminate interferences from groundwater samples.

TABLE 7

| Sample U (µg/L) | Sample Volume (mL) | Equivalent Uranium (µg/L) | Color | Expected Color |
|---|---|---|---|---|
| 20.9 | 20 | 0.4 | Tan | Yellow |
| 140.2 | 20 | 2.8 | Purple | Gray |
| 20.9 | 1000 | 20.9 | Purple | Purple |

Example 7

A procedure for determining uranium content in groundwater or drinking water as described herein can be carried out utilizing a URALIX column purchased from Institut de Radioprotection et de Sûreté Nucléaire DRPH/SDI/LRC BP 17; 92262 Fontenay aux Roses Cedex; France.

Initially the column as obtained can be conditioned for concentration of uranium from a groundwater or drinking water sample according to the following procedure:

Discard solution in column when shipped
Pass 10 mL of 1 M $HNO_3$ through the column
Pass 100 mL of 0.04 M $NaNO_3$ pH 5 through the column
Pass 100 mL of 0.3 M acetate buffer pH 5 through the column
Check the pH of collected solution to make sure the pH is at 5. If the pH is not at 5 then pass 10 mL of acetate buffer through the column. The pH of the solution coming of the column must be between 5.0 and 5.3 before proceeding.

A sample to be run through the URALIX solid-phase extraction column can be prepared by adjusting the pH of the sample to 5 immediately before loading the sample onto the column, if necessary.

For example, pH can be increased to 5 through use of 20% $NH_4OH$ with use of 3% $NH_4OH$ as the pH approaches 5. If the pH exceeds 5, it can be brought down using 1 M HCl. The pH of the sample must be between 5.0 and 5.3 before running a sample according to this method. pH can be checked with a pH meter, litmus paper, or any other pH indicator.

To wash the column, 10 mL of 8 M $HNO_3$ can be passed through the column.

To recondition a column following use, 100 mL of 0.04 M $NaNO_3$ can be passed through the column.

One exemplary experimental procedure is outlined below. It should be understood, however, that the present disclosure is not limited to this exemplary solid-phase extraction process.

Condition column
Prepare sample
Load sample onto column
Pass 10 mL of 0.04 M $NaNO_3$ pH 5 through the column
Discard solution
Consecutively pass 3-10 mL of 8 M $HNO_3$ through the column
Collect the effluent
Evaporate the 30 mL of effluent to dryness
Add 3 mL of 1 M $HNO_3$
Add 3 mL of $10^{-5}$ M Br-PADAP
Add 2 mL of TEA buffer
Add 2 mL of 0.02 M NaF
Add 400 µm of 11.1 M $NH_4OH$ If a column is to be reused, it can be washed and reconditioned, for instance according to previously described methods. A column can be reused several times, for instance, about 3 to about 5 times, if desired.

It will be appreciated that the foregoing examples, given for purposes of illustration, are not to be construed as limiting the scope of this disclosure. Although only a few exemplary embodiments have been described in detail above, those skilled in the art will readily appreciate that many modifications are possible in the exemplary embodiments without materially departing from the novel teachings and advantages of this disclosure. Accordingly, all such modifications are intended to be included within the scope of this disclosure as defined in the following claims and all equivalents thereto. Further, it is recognized that many embodiments may be conceived that do not achieve all of the advantages of some embodiments, yet the absence of a particular advantage shall not be construed to necessarily mean that such an embodiment is outside the scope of the presently disclosed subject matter.

What is claimed is:

1. A method for determining the presence or quantity of uranium in an aqueous test sample, the method comprising:
    concentrating the uranium in the aqueous test sample, wherein the step of concentrating the uranium is comprised of:
        a) binding the uranium to an extractant to form a uranium/extractant complex,
        b) separating the uranium from the extractant by use of a separation agent, interaction between the uranium/extractant complex and the separation agent forming a first complex comprising the uranium, the first complex being more favorable chemically than the uranium/extractant complex; and
        c) interacting the first complex with a compound to form a second complex comprising the uranium;
    following the step of concentrating the uranium, interacting the second complex with a detectable substance to form a uranium/detectable substance complex, the uranium/detectable substance complex being more favorable chemically than the second complex; and
    detecting the complex of the uranium and the detectable substance to obtain information with regard to the presence or quantity of the uranium in the aqueous test sample.

2. The method according to claim 1, further comprising removal of metals other than uranium from the aqueous test sample.

3. The method according to claim 1, wherein the concentrating step comprises a solvent-based extraction chromatography process.

4. The method according to claim 1, wherein the concentrating step comprises a solid-phase extraction chromatography process.

5. The method according to claim 1, wherein the concentrating step comprises a liquid-liquid extraction process.

6. The method according to claim 1, further comprising comparing the visibly detected complex with calibration data.

7. The method according to claim 1, further comprising pretreating the aqueous test sample.

8. The method according to claim 1, the method further comprising separating one or more metals other than uranium from the extractant prior to separating the uranium from the extractant.

9. The method according to claim 1, wherein the first complex is a uranyl carbonate complex.

10. The method according to claim 1, wherein the complex of the uranium and the detectable substance is visibly detected.

11. The method according to claim 1, wherein the aqueous test sample is natural water.

12. The method according to claim 11, wherein the aqueous test sample is drinking water.

13. The method according to claim 1, wherein the second complex is a uranyl nitrate complex.

14. The system according to claim 13, wherein the separation agent is sodium carbonate or sodium bicarbonate.

15. The method according to claim 1, wherein the second complex comprising the uranium is formed according to a process that includes boiling a solution comprising the first complex and nitric acid.

16. The system according to claim 15, wherein the compound is nitric acid.

17. A system for detecting the presence or quantity of uranium in an aqueous test sample, the system comprising:
- an extraction chromatography column comprising an extractant for binding uranium;
- a separation agent that interacts with uranium on the extraction chromatography column to remove uranium from the extractant and form a first complex comprising the uranium;
- a compound that interacts with the first complex to form a second complex comprising the uranium; and
- a detectable substance that interacts with the second complex to form a detectable complex with uranium; wherein
the system is a portable test system.

18. The system of claim 17, the extraction chromatography column comprising the extractant directly bound to a support phase.

19. The system of claim 17, the extraction chromatography column comprising the extractant dissolved in a liquid extraction medium, the liquid extraction medium comprising an organic solvent.

20. The system of claim 17, wherein the detectable substance is Br-PADAP.

21. The system of claim 17, wherein the extractant is selected from the group consisting of a diamyl amylphosphonate extractant, a dyglycolamide extractant, a phosphonic acid extractant, a tricarboxylic calix[6]arene, and a trishydroxamic calix[6] arene.

22. The system according to claim 17, wherein the first complex is a uranyl carbonate complex.

23. The system according to claim 17, wherein the second complex is a uranyl nitrate complex.

24. The system according to claim 17, wherein the detectable complex is visibly detectable.

25. The system of claim 17, the extraction chromatography column comprising a stationary phase held on a support phase, the stationary phase comprising the extractant that binds uranium.

26. The system of claim 25, wherein the stationary phase is impregnated within pores of the support phase.

27. The system of claim 17, further comprising a treatment reagent.

28. The system of claim 27, wherein the treatment reagent is a pH modifier.

29. The system of claim 27, wherein the treatment reagent reacts with a metal of the aqueous test sample, the metal being a metal other than uranium.

* * * * *

UNITED STATES PATENT AND TRADEMARK OFFICE
CERTIFICATE OF CORRECTION

PATENT NO. : 8,133,740 B1  
APPLICATION NO. : 12/543856  
DATED : March 13, 2012  
INVENTOR(S) : Timothy A. DeVol, Amy E. Hixon and David P. DiPrete It is certified that error appears in the above-identified patent and that said Letters Patent is hereby corrected as shown below:

In the Claims

Column 18, line 44 "comparing the visibly detected complex with calibration data." should read --comparing the detected complex with calibration data.--

Signed and Sealed this  
Thirtieth Day of September, 2014

Michelle K. Lee  
*Deputy Director of the United States Patent and Trademark Office*

UNITED STATES PATENT AND TRADEMARK OFFICE
CERTIFICATE OF CORRECTION

PATENT NO. : 8,133,740 B1  
APPLICATION NO. : 12/543856  
DATED : March 13, 2012  
INVENTOR(S) : Timothy A. DeVol et al.

It is certified that error appears in the above-identified patent and that said Letters Patent is hereby corrected as shown below:

Specification

Column 1, lines 14 - 16 states,

"The United States Government may have rights in this disclosure pursuant to U.S. Department of Energy Grant Number DE-FG02-07ER64411 ."

Please correct this paragraph to read as follows:

-- This invention was made with government support under grant numbers DE-FG02-07ER64411 and DE-FG07-05ID14692 awarded by the U.S. Department of Energy. The government has certain rights in the invention. --

Signed and Sealed this  
Twelfth Day of January, 2016

Michelle K. Lee  
*Director of the United States Patent and Trademark Office*